(12) United States Patent
Cocchietto et al.

(10) Patent No.: US 8,545,739 B2
(45) Date of Patent: Oct. 1, 2013

(54) METHOD AND APPARATUS FOR PREPARING MICRO-PARTICLES OF POLYSACCHARIDES

(76) Inventors: Moreno Cocchietto, Trieste (IT); Dario Voinovich, Trieste (IT); Laura Zorzin, Fiumicello (IT); Gianni Sava, Trieste (IT)

(*) Notice: Subject to any disclaimer, the term of this patent is extended or adjusted under 35 U.S.C. 154(b) by 48 days.

(21) Appl. No.: 13/393,569

(22) PCT Filed: Sep. 2, 2010

(86) PCT No.: PCT/EP2010/062865
§ 371 (c)(1),
(2), (4) Date: Mar. 1, 2012

(87) PCT Pub. No.: WO2011/026896
PCT Pub. Date: Mar. 10, 2011

(65) Prior Publication Data
US 2012/0161346 A1    Jun. 28, 2012

(30) Foreign Application Priority Data

Sep. 2, 2009   (IT) .............................. PD2009A0249

(51) Int. Cl.
*B29B 9/00*        (2006.01)
(52) U.S. Cl.
USPC ........... 264/9; 264/13; 264/14; 425/6; 425/10

(58) Field of Classification Search
None
See application file for complete search history.

(56) References Cited

U.S. PATENT DOCUMENTS

| | | | | |
|---|---|---|---|---|
| 5,047,180 | A | * | 9/1991 | Steiner et al. ..................... 264/5 |
| 5,244,984 | A | * | 9/1993 | Suzuki ........................... 525/432 |
| 5,716,551 | A | * | 2/1998 | Unruh et al. ................... 252/500 |

FOREIGN PATENT DOCUMENTS

| | | |
|---|---|---|
| DE | 19619811 A1 | 1/1998 |
| WO | 2006/093972 A2 | 9/2006 |
| WO | 2007/070957 A1 | 6/2007 |

OTHER PUBLICATIONS

International Search Report from corresponding PCT/EP2010/062865 dated Oct. 2, 2011; 3 pgs.

* cited by examiner

*Primary Examiner* — Mary F Theisen
(74) *Attorney, Agent, or Firm* — Gifford, Krass, Sprinkle, Anderson & Citkowski, P.C.

(57) ABSTRACT

The present invention relates to a method for the production of micro-particles of polysaccharides. The method includes preparing a feeding solution and a gelifying liquid to collect nebulized jets of the feeding solution. The feeding solution contains at least one polymer capable of forming micro-particle structures and at least one biologically active substance. The feeding solution is pressurized inside an air-less nebulizing unit and then nebulized through the unit itself so as to generate nebulized jets impacting the surface of the gelifying liquid.

14 Claims, 15 Drawing Sheets

METHOD AND APPARATUS FOR PREPARING MICRO-PARTICLES OF POLYSACCHARIDES

CROSS-REFERENCE TO RELATED APPLICATIONS

This application is the U.S. National Phase of PCT/EP2010/062865 filed Sep. 2, 2010, which claims priority of Italian Patent Application PD2009A000249 filed Sep. 2, 2009.

FIELD OF THE INVENTION

The present invention relates to a method and apparatus for the production of micro-particles of polysaccharides. More precisely, the invention relates to a method and apparatus for preparing micro-particles from an aqueous solution, suspension or emulsion containing at least one polymer capable of forming micro-particle structures and at least one biologically active substance, usefully employable for applications in alimentary, pharmaceutical, cosmetic, chemical and agricultural fields.

STATE OF THE ART

In order to effectively deliver oral therapeutic agents, such as for example proteins and peptides, since a long time the research has been directed to the preparation of micro-particles capable of incorporating and releasing these agents in a controlled manner. Among the polymers employable for preparing the micro-particles, natural polysaccharides such as starch, k-carrageenan, alginate, agar, agarose, dextran and chitosan are particularly interesting because of their physico-chemical properties and their high biocompatibility and bio-degradability. Indeed, polysaccharides are non-toxic polymers, which may form gel structures, where therapeutic, or otherwise biologically active agents, even with high molecular weight may be incorporated. Moreover, polysaccharides are known to have bio-adhesive properties, which feature is particularly important for a therapeutically effective absorption of the incorporated active ingredients through the intestinal mucosa.

The research developed different techniques for the production of micro-particles of polysaccharides. In patent application WO 2005/013941, there is described for example a process for preparing microcapsules incorporating a biologically active substance from an alginate solution at concentrations from 2 to 4% w/v, gelled with solutions of divalent ions by emulsification into a shaft stirrer. However, the practice demonstrated that such a technique allows to produce a few grams/day of micro-particles, with high production costs. Accordingly, such a technique is only adapted to produce small batches of micro-particles substantially suitable for experimental and not large-scale applicable usage.

In addition to the above description, the production process in the cited patent application includes the employ of surfactants for obtaining particles into the emulsion and isopropyl alcohol for removing the oil therefrom. Using such an alcohol over long times is not recommended in the view of operator's health, as the isopropanol may be irritating for the respiratory system mucosae and eyes.

In addition to the above-described technique, other techniques for the production of micro-particles of polysaccharides are known. One of these is based on the employ of compressed air or steam for carrying out the nebulization of a feeding solution containing a polymer and a biologically active substance. More precisely, such a solution is nebulized through a nebulization unit placed in a position on the top of a micro-incapsulation chamber, in which a collection liquor is contained. In the nebulization unit, a pressurized solution flow and a compressed air flow converge. A plurality of needles carries out the nebulization of the solution in the presence of compressed air.

An example of a nebulization unit of this type is described in patent application WO 01/45519, for example. More precisely, in this example, the nebulization unit comprises one or more needles from which the feeding solution exits, which solution is nebulized through a pressurized air flow as soon as the solution reaches the exit orifice of the needles. The practice demonstrated that this production technique poorly aids the preparation of micro particles with particularly viscous feeding solutions. In other words, this technique is effective only if the viscosity of the solutions is within a narrow range and in any case it is generally below 2 Pa·s. Another drawback of this procedure is the employ of high pressure flows for nebulizing the feeding solution. Indeed, these flows necessarily require extended and so costly facility dimensions. Furthermore, the air exiting from the needles along with drops of feeding solution disadvantageously impact the surface of the gelifying liquid, thus creating a trouble to the process of forming the micro-particles.

Other known production techniques process the feeding solution by means of others systems, for example of electromagnetic or piezoelectric type as in the case of the so-called laminar-jet break up technique. In others cases, ultrasounds systems (prilling), or systems based on electric potential differences (high voltage driven) are used. All these techniques proved to be very little advantageous, as in view of high economical investment, they allow to process relatively small volumes of feeding solution, containing a polysaccharide and a biologically active substance to be incapsulated, within a very narrow range of viscosity. Accordingly, there is a need of alternative technical solutions which allow to overcome the limits of the current methods employed for the production of micro-particles of polysaccharides.

SUMMARY

It is the task of the present invention to provide a method and apparatus for the production of micro-particles comprising at least one biologically active substance from a feeding solution, containing at least one polymer capable of forming micro-particle structures and at least one biologically active substance. Within this task, it is an object of the present invention to provide a method and apparatus for the production of micro-particles of polysaccharides comprising at least one biologically active substance from a feeding solution, the viscosity of which may vary in a wider range of values than that currently processable by means of known techniques. It is another object of the present invention to provide a method and apparatus capable of allowing a higher productivity than that of the traditional facilities, while ensuring a high level of quality of the final product. It is a further object to provide a method and apparatus for the production of micro-particles which are reliable, relatively easy to be implemented/carried out at relatively low costs.

The method for preparing micro-particles of polysaccharides comprising at least one biologically active substance according to the invention includes to prepare a feeding solution and a gelifying liquid to collect nebulized jets of the feeding solution. More precisely, the term "feeding solution" generally means a solution, suspension or emulsion (also micro-emulsion or nano-emulsion) containing at least one polymer (preferably alginate or alginate in combination with hydroxypropylmethylcellulose HPMC) having characteristics such that it is prone to subsequently obtain micro-particles by gelification. The feeding solution further contains at least one biologically active substance (for example lysozyme) which will be then incorporated into the polymeric micro-particles due to the polysaccharide gelification. The gelifying liquid contains at least gelifying substances (such as for example aqueous solutions of divalent ions and in particular $CaCl_2$) in order to generate micro-particles by gelification. Such a gelifying solution may also optionally comprise a further polysaccharide, capable of forming a coating on the micro-particles obtained by nebulization. According to an alternative solution, such a coating process may also be actuated on the micro-particles, formed by at least one polysaccharide in which at least one biologically active substance is incorporated, obtained after a first gelification with a gelifying agent and separated from such a first gelification solution by mixing with a coating solution comprising at least a further polysaccharide and a divalent ion. Preferably, in this case, the polysaccharide is chitosan and the divalent ion is $Ca^{2+}$.

The method according to the invention includes pressurizing the feeding solution inside an air-less nebulizing unit and nebulizing the solution itself by means of such a unit so as to generate micro-drop jets (hereinafter also referred to as nebulized jets), impacting the surface of the gelifying liquid. For the purposes of the present invention, the term "air-less" means a nebulizing unit which ensures the nebulization of the feeding solution without a concurrent air leakage from the unit itself. In other words, nebulization is actuated without mixing the air overall size of the production facility, thus ensuring both a more accurate and less turbulent production of the nebulized and a more manageable, cleaner and less turbulent process for the production of micro-particles in limited spaces. In addition, the absence of output air during the nebulization allows to use higher working pressures. This results in the possibility of processing viscous, dense feeding solutions in contrast with the traditional production processes with comparable overall dimensions.

The feeding solution is preferably pre-arranged inside a reservoir and pressurized inside the air-less nebulizing unit through a pneumatically-operated pump. The nebulizing unit is actuated by means of a pneumatic circuit in which pressurized, preferably treated air circulates. In particular, the pressurized air is preferably dried to eliminate the existing moisture and/or filtered to retain the existing residual oil and/or water. This solution advantageously avoids moisture drops, lubricating oil and possible other waste from flowing in the production system and in the product, which will deteriorate the micro-particles quality.

The nebulizing unit is preferably actuated in a pulsed mode, i.e. so that the nebulized jets have a predetermined length and frequency. It has been observed that by means of a proper regulation of pulses length and frequency the process of gelifying and coating (hereinafter also referred to as coating) the feeding solution in the gelifying liquid, i.e. forming micro-particles, is advantageously optimized.

According to another aspect of the present invention, the pneumatically operated pump employed to pressurize the feeding solution is also advantageously actuated by means of the same pneumatic circuit, which actuates the nebulizing unit. In other words, the pump is also actuated by employing treated air. This solution proves to be particularly effective in terms of production savings.

According to another aspect of the present invention, the gelifying liquid is preferably arranged inside a gelification chamber, which is maintained in motion when nebulizing the feeding solution. It has been observed that this expedient allows a better distribution of nebulized micro-drops on the surface of the gelifying liquid, since the micro-particles are avoided from forming again in the same point, with consequent and not predictable aggregation processes therebetween. The gelification chamber is preferably moved by moving means, which allow an adjustable-speed rotation thereof. Alternativey, these means could be configured so as to subject the chamber to an alternating rectilinear motion or even to a cyclic movement along a predetermined path.

The present invention also relates to an apparatus through which the method according to the present invention is carried out. The apparatus according to the invention comprises a reservoir and at least one micro-incapsulation chamber by gelification, intended to contain the feeding solution and the gelifying liquid, respectively. The apparatus is characterized in that it comprises an air-less type nebulizing unit operated by means of a first pneumatic flow. The nebulizing unit is hydraulically connected to the reservoir through a pneumatically-operated pump, which is operated by means of a second pneumatic flow, for pressurizing the feeding solution prior to nebulization.

According to a first aspect of the present invention, the apparatus comprises regulating means, comprising a solenoid valve timing, for example, to adjust the length and frequency of the first pneumatic flow intended to operate the nebulizing unit so that it nebulizes according to a pulsed mode. The unit is provided with a interchangeable nozzle which defines the configuration of the nebulized jets. Such a nozzle is preferably ellipsoidal in section, so as to generate nebulized jets substantially ellipsoidal in section.

The gelification chamber is preferably placed on a platform taken and preferably maintained in rotation when nebulizing the feeding solution through direction and speed-adjustable moving means.

According to a further, advantageous aspect of the present invention, the apparatus comprises a compressed air unit to generate said first and said flow of compressed air in series at which a unit for air processing is pre-arranged. The latter preferably comprises a drying unit in series at which an air filtering station is placed.

BRIEF DESCRIPTION OF THE DRAWINGS

Further featured and advantages will become apparent during the detailed description of a method and apparatus according to the present invention illustrated by way of non-limitative example in the accompanying drawings in which.

DETAILED DESCRIPTION OF THE INVENTION

The features and advantages of the present invention will be better understood from the following description, in which preferred embodiments of the apparatus will be described along with examples of possible applications.

Figure 1:
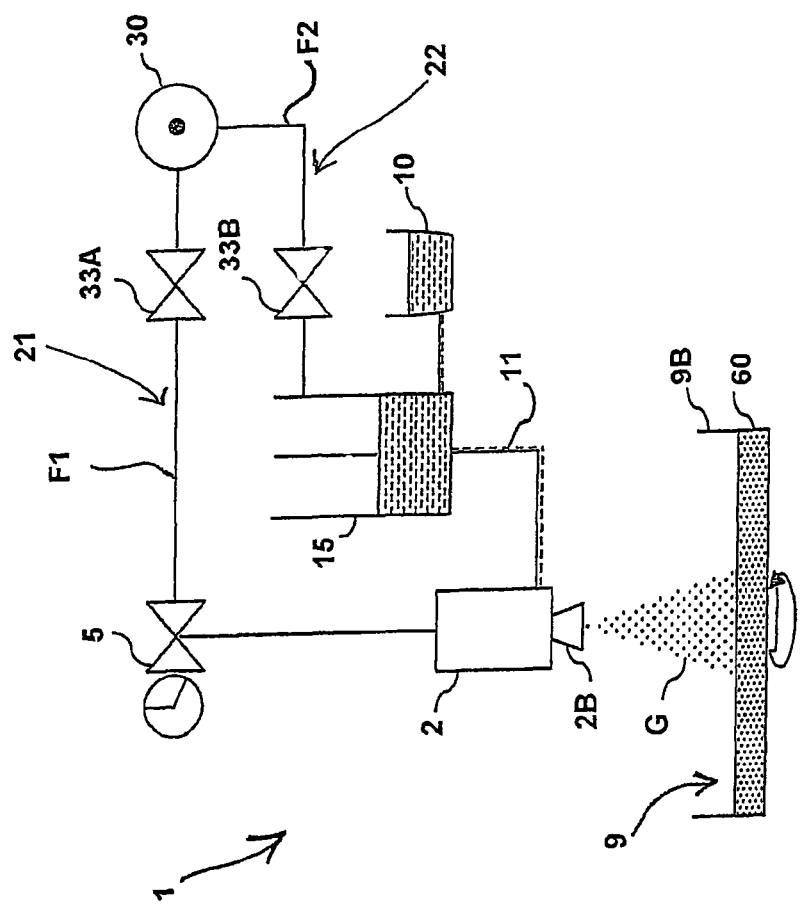
FIG. 1 is a first schematic view of a first possible embodiment of an apparatus according to the present invention.

FIG. 1 is a schematic view illustrating a possible embodiment of an apparatus for the production of polysaccharides according to the invention. Apparatus 1 comprises a reservoir 10 intended to contain a "feeding solution". As indicated above by this term, it generally means a solution, suspension or emulsion (also micro-emulsion o nano-emulsion) containing at least one polymer (for example alginate o alginate combined with hydroxypropylmethylcellulose HPMC) having features such that it is prone to subsequently obtain micro-particles, preferably by gelification of such a polymer or mixture of polymers. The feeding solution preferably also contains at least one biologically active substance (for example lysozyme) which will be then incorporated into the polymeric micro-particles.

Apparatus 1 comprises at least one chamber 9 of micro-incapsulation of the biologically active substance by gelification intended to contain a collection gelifying liquid. The latter serves the function of collecting nebulized jets G consisting of feeding solution micro-drops and generated according to modes described hereinafter in detail. More precisely, the gelifying liquid is used for the process of gelification of the micronized through the presence of a gelifying agent in the liquid, such as a divalent ion salt, for example $CaCl_2$ at a proper concentration. Optionally, in an alternative embodiment, apparatus 1 may also comprise another chamber 60B for coating the micro-particles formed upon the nebulization and the subsequent gelification. In detail, in such a chamber 60B a liquid may be pre-arranged, containing a further polymer (for example chitosan) and/or other substances capable of forming a coating, by a further gelification of such a polymer on the micro-particles obtained by means of nebulization and first gelification.

Upstream of the first gelification chamber 9, apparatus 1 according to the invention comprises an air-less nebulizing unit 2, this term meaning a unit capable of generating nebulized jets by only using the pressure of the feeding solution and especially without using the mixture of the latter with pressurized air. The nebulizing unit 2 is actuated by means of a first pneumatic flow F1, i.e. a first flow of pressurized air. The same unit 2 is further connected to reservoir 10 through a hydraulic circuit 11 along which a pump 15 is also placed for pressurizing the feeding solution contained in the reservoir. Pump 15 is actuated by means of a second pneumatic flow F2, i.e. a second flow of pressurized air. The first air flow F1 and the second flow F2 circulate inside a first branch 21 and a second branch 22, respectively, of a pneumatic circuit powered by a pressurized air source, which preferably consists of a generating unit 30 comprising a plunger compressor, for example.

Figure 2:
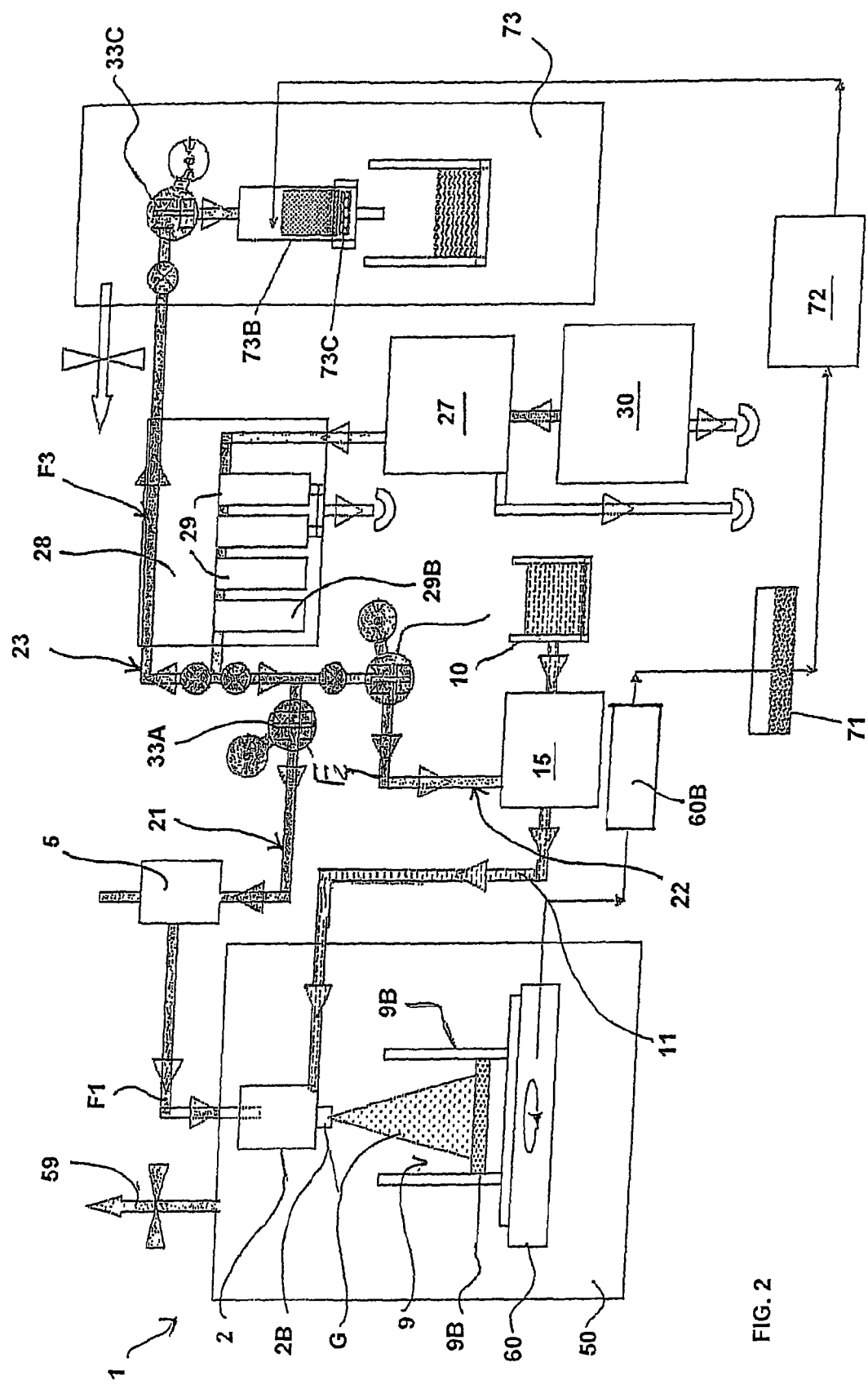
FIG. 2 is a second schematic view of the apparatus in FIG. 1.
Figure 3:
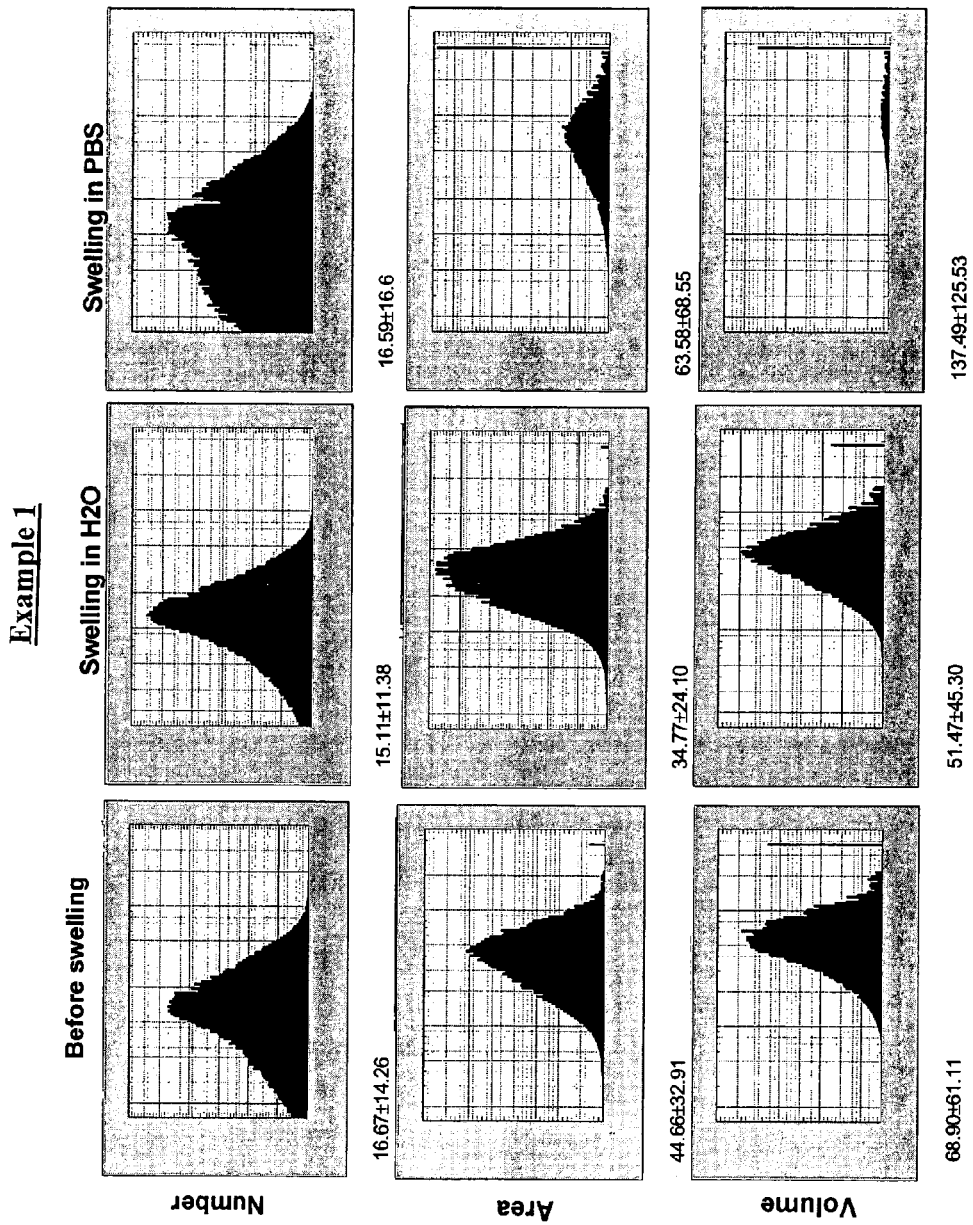
FIG. 3 shows a diagram related to the statistical distribution of area, volume and number values of a first batch of particles obtained by means of an apparatus according to the present invention.
Figure 4:
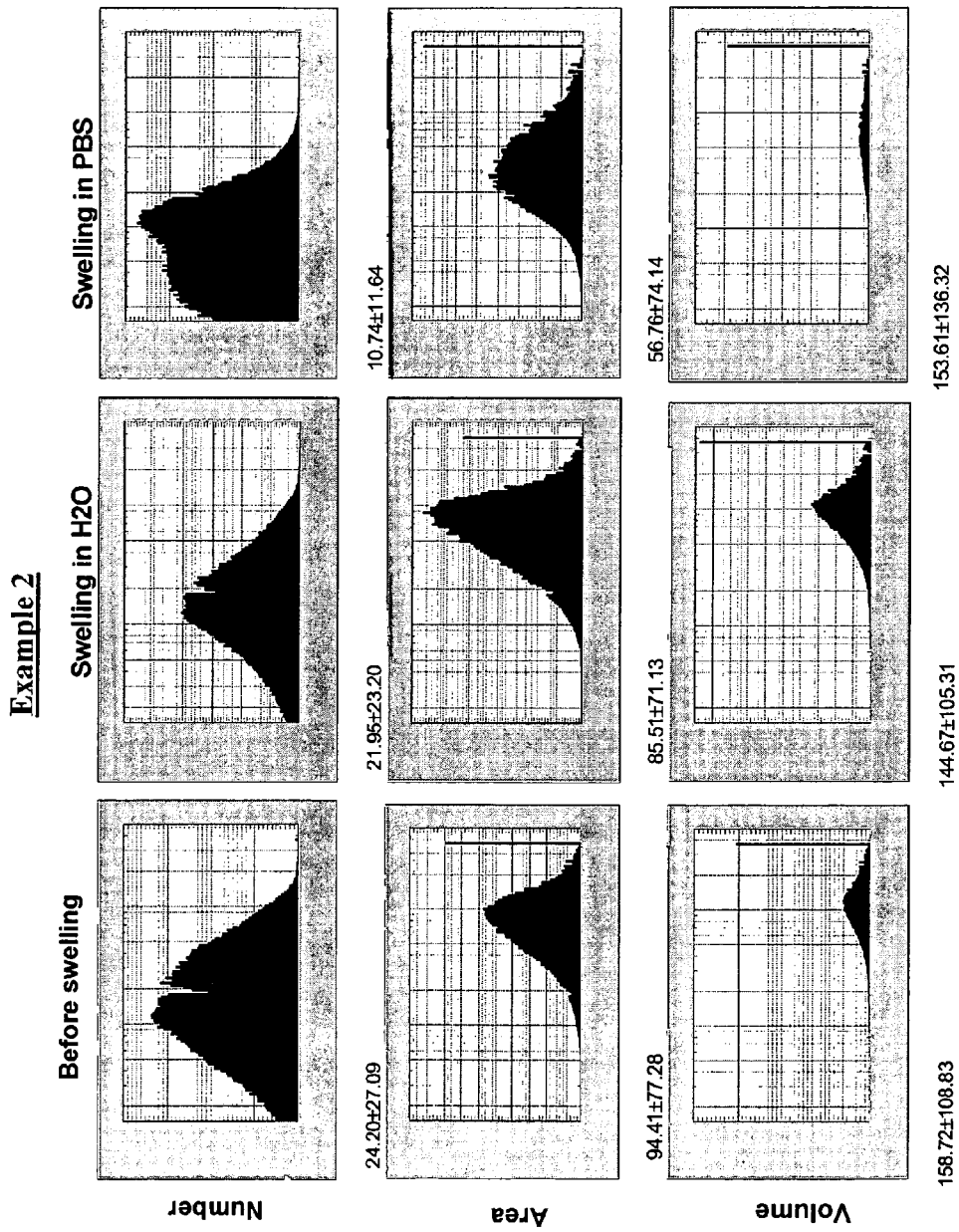
FIG. 4 shows a diagram related to the statistical distribution of area, volume and number values of a second batch of particles obtained by means of an apparatus according to the present invention.
Figure 5:
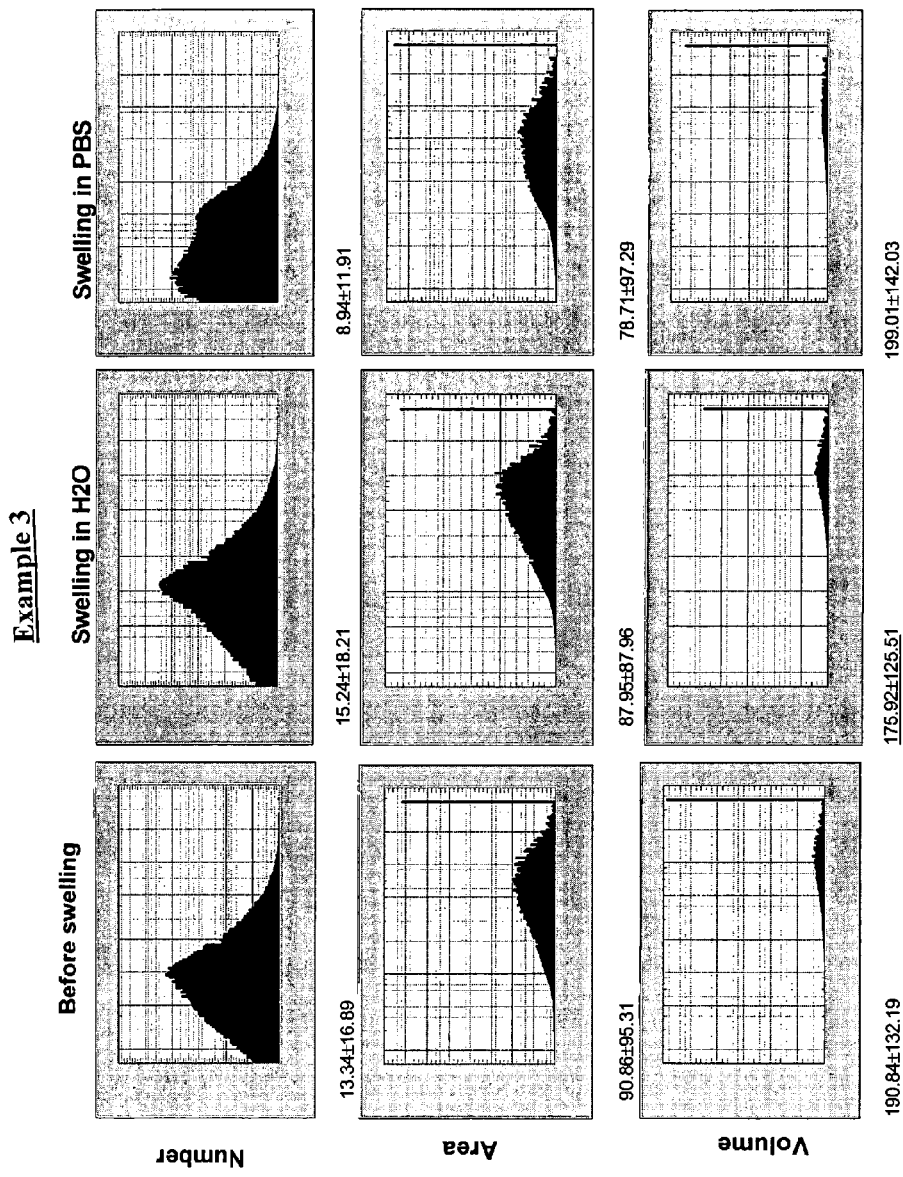
FIG. 5 shows a diagram related to the statistical distribution of area, volume and number values of a third batch of particles obtained by means of an apparatus according to the present invention.
Figure 6:
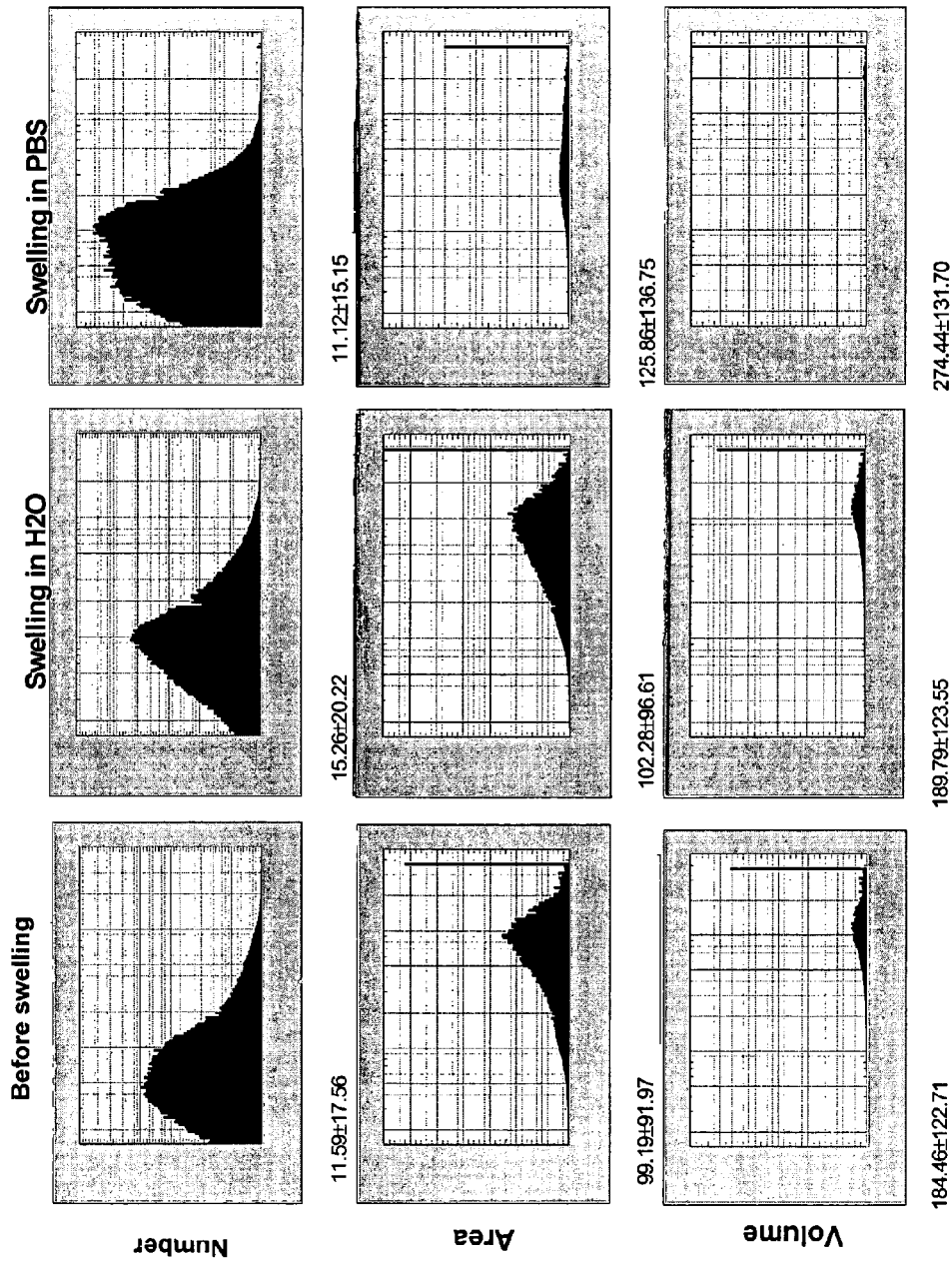
FIG. 6 shows a diagram related to the statistical distribution of area, volume and number values of a fourth batch of particles obtained by means of an apparatus according to the present invention.

With reference to the schematic view in FIG. 2, downstream of the generating unit, a unit for processing the air is preferably placed, which preferably comprises a drying unit 27 and a filtering station 28. The drying unit 27 serves the function of dehumidifying the air, which then crosses the filtering unit 28 preferably comprising a plurality of filters 29 capable of retaining oil, residual water, and other impurities. As mentioned above, the air treatment in the filtering station 28 advantageously avoids moisture drops, lubricating oil and other possible waste from entering the productive system and the product, which would deteriorate the product quality and reduce the apparatus integrity. Preferably, the filtering station 28 also comprise an activated carbon filter 29B in order to use air free from chemical and/or biological impurities present in the motes.

Downstream of the unit of the filtering station 28 the pneumatic circuit branches into the first branch 21 and into the second branch 22 through which the flows F1 and F2 are taken to nebulizing unit 2 and pump 15, respectively, to allow their related operation. As shown, two flow regulators 33A, 33B are each pre-arranged on a corresponding branch 21, 22 of the circuit to adjust the pressure of the corresponding flow F1 and F2. In particular, the regulator 33B related to the second branch 22 adjusts the pressure level of the air directed to pump 15, that is the pressure level at which the feeding solution is taken to the nebulizing unit 2.

As apparent from FIG. 1, the first flow F1 is intercepted by regulating means, which time its passage towards the nebulizing unit 2. In other words, these means regulate the flow length and frequency so that they actuate the nebulizing unit 2 in a pulsed mode. As mentioned above, the proper regulation of the nebulization length and frequency allow to optimize the process of "gelification" and "coating" within the gelification chamber 9. In detail, in the schematic solution in FIG. 1, the regulating means comprises a solenoid valve timer 5 which intercepts the first flow F1 before its entry into unit 2.

The nebulizing unit 2 is provided with an orifice from which the feeding solution may exit in a nebulized form. An interchangeable nozzle 2B is connected to the nebulizing unit 2 at the orifice for defining the shape of the nebulized jet. In particular, the shape of the nozzle 2B determines the angle, the spraying volume, the shape of micronized jet, and the size of solution micro-drops forming the jet. It has been shown that for the purposes of the invention, employing a nozzle 2B configured so as to generate nebulized jets which are ellipsoidal in section is particularly effective. Possible examples of applications of the apparatus will be disclosed below, in which the nebulization nozzle 2B is substantially ellipsoidal in shape.

The nebulizing unit 2 and the gelification chamber 9 are preferably placed inside a chemical hood 50 provided with a suction element 59 for aspirating the portion of micronized (i.e. of nebulized jet) which does not impact the surface of the gelifying liquid. This solution allows to advantageously improve the control of the gelification process. It has been observed that the nebulizing unit 2 is arranged so that the nebulization nozzle 2B is placed substantially above the gelification chamber 9. Thereby, the nebulized jets may effectively impact the surface of the gelifying liquid, thus uniformly spreading thereon.

In the solution shown, the gelification chamber 9 consists of a vessel 9B which is placed on a platform 60 in turn moved by suitable moving means. More precisely, the latter are preferably configured so as to determine a rotation of the gelification chamber 9 at adjustable speed and rotation direction. Through this solution, the micronized jets impact the surface of the liquid in different points so that the process of forming micro-particles occurs in different points, thus using the surface of the gelifying liquid as much as possible.

The schematic view in FIG. 2 shows a preferred embodiment of the apparatus according to the invention which comprises a system for the post-gelification treatment of the semi-finished product represented in fact by the gelifying liquid in which the micro-particles are suspended, formed upon the impact of the nebulized jets on the surface of the liquid itself. Such a semi-finished product is first treated in a sieve unit 71 to eliminate possible debris produced during the nebulization/gelification process. Therefore, the treatment system comprises a centrifugal unit 72 in which the sieved liquid is poured for recovering the micro-particles and eliminating the gelificant solution. The latter is removed by centrifugation, thus separating the micro-particles which are in the form of agglomerates. These are suspended again and washed preferably more than once, for example with ethyl alcohol, by further centrifugations for dehydrating the agglomerates.

Finally, the treatment system includes a filtration unit 73 for partially recovering and drying and for recovering most of the alcohol. Such a unit preferably comprises a chamber 73B which contains a high-strength filter 73C made of polypropylene with a cut-off, e.g. of 30 microns. The micro-particle agglomerates are suspended again in alcohol in the chamber 73B and then filtered employing a third compressed air flow F3 also advantageously generated by the generation unit 30. In this regard, a third pneumatic circuit 23 conveys the pressurized air exiting from the treatment unit to the filtration unit 73. Also in this case, the presence of a flow regulator 33° C. will allow the working pressure of such a third flow F3 to be adjusted.

A typical production cycle implementable by means of the above-described apparatus 1 schematized in FIG. 2 will be disclosed below. The accomplishment of each production cycle includes a preliminary cleaning of the facility. In particular, reservoir 1 is first filled with water. Timer 5 is then adjusted so as to set a wash pulse sequence (for example with a length from 2 and 7 seconds and a relatively short frequency from 0.2 and 2.2 sec). Then, under the nebulizing unit 2, before the nozzle 2B a relatively large vessel is placed. The flow regulator 33B of the second circuit 22 is rotated so as to increase the water pressure in the hydraulic circuit 11 until splashes of enough power to clean the same hydraulic circuit are obtained, but without the splashes exiting from the vessel. At this point, water is poured in the hydraulic circuit until it exits clear and the reservoir is substantially emptied.

The described step of cleaning is normally carried out at the end of the daily session or if there are pauses longer than one hour. Also, the cleaning is carried out when incompatible feeding solutions are to be processed. On the contrary, if during the daily working session the same feeding solution is used (or one reasonably compatible, e.g. the same feeding solution but with a different concentration of one or more components), the cleaning may also be not carried out.

After this preliminary cleaning step, timer 5 is turned off and the pressure of pneumatic flows F1 and F2 is taken to zero. Reservoir 1 is filled with the feeding solution. The timer is set again. The pressure of the second flow F2 is increased until the pump 15 is operated. As soon as the feeding solution starts to exit, the timer is turned off again and the nozzle 2B is installed in the nebulizing unit 2. Timer 5 is then set so as to have a slower nebulization frequency (about every 1 or 2 seconds). At this point, the second regulator 33B is set to a pressure directly depending on the viscosity of the feeding solution.

Then, the gelification chamber is placed under the nebulizing unit 2 and filled with gelifying liquid. The rotation speed of the gelification chamber is then set and the pulse nebulization of the feeding solution is then started in order to reach the gelification of the micro-drops of the solution itself inside the gelifying liquid. Once a single production cycle has been concluded, the semi-finished product is then processed in the above-described treatment system.

Some examples of the production of micro-particles are disclosed below, which micro-particles are prepared by gelifying sodium alginate according to the method of the present invention and by means of the above-described apparatus. Two separate feeding solutions, characterized by very different viscosities (2 Pa·s and 100 Pa·s) were prepared from a solution of alginate of 2% w/v and 4% w/v, respectively (which, for convenience, are referred to as "lower viscosity" and "higher viscosity" below). These feeding solutions have been nebulized with the aid of two different nozzles 2B but both ellipsoidal in shape, applied to the nebulizing unit 2 (hereinafter referred to as "lower size nozzle" and "higher size nozzle"), having a total of 4 final separate micro-particle products.

Example 1

Application of the apparatus according to the invention for preparing a micro-particulate obtained by gelification, micronizing a feeding solution having a higher degree of viscosity with an orifice of smaller size.

A first aqueous/alcoholic solution of 0.4% w/v hydroxypropylmethylcellulose (HPMC) (Cigenmann-Veronelli; Milan) was prepared, in which for each liter of solution, 4 g of HPMC were dissoluted in 400 ml of absolute ethyl alcohol (EtOH) and then 600 ml of water were added. A second aqueous solution of 1% w/v lysozyme (Belovo; Belgium) and 4% w/v sodium alginate (Quinsdao; Cina) was prepared, in which for each liter of solution, 10 g of lysozyme were dissolved in 1 litre of distilled water; 40 g of sodium alginate (Quinsdao; China) were then added and dispersed in solution by homogenization. A feeding solution (hereinafter indicated by C) was then prepared, in which for each liter of solution, 547 ml of solution A were mixed to 453 ml of solution B. A collecting liquid was then pre-arranged in the gelification unit (hereinafter referred to as solution D) consisting of an aqueous solution of 0.1% w/v chitosan (Quinsdao, China) and 15% w/v anhydrous $CaCl_2$ (Carlo Erba), in which for each liter of solution D, 1 g of chitosan was dissolved in one liter of water acidified with 2.5% v/v acetic acid. 150 g of anhydrous $CaCl_2$ were then added and solubilized.

Set-Up Condition of the Apparatus:
Feeding solution volume: 1 liter,
Collecting liquid volume: 1.5 liter,
Nebulization orifice: 0.20 mm (smaller diameter).
Height of nebulization spread: 30 cm,
Input pressure of the nebulizing unit: 4 bars,
Feeding solution pump pressure: 1.5 bars,
Timing conditions:
nebulization pulse length: 0.5 sec,
pause between two nebulization pulses: 3 sec,
Gelification chamber rotation speed: 35 rpm.
The nebulization of the feeding solution was conducted through the above-described facility. The collecting liquid (solution D) was prepared in the gelification chamber. Then, the pneumatic circuits were opened and the process of nebulization started by setting the above-indicated pressure and timing values. One liter of feeding solution was nebulized during a period of 30 minutes. At the end of the process, a semi-finished product consisting of micro-particles of calcium alginate, HPMC and chitosan containing lysozyme, suspended in the solution D, was obtained. The semi-finished product was then treated to obtain a dry product. More precisely, the semi-finished product was subjected in series to centrifugation, washings in absolute ethanol, pressurized filtration and drying at 37° C.

Example 2

Application of the apparatus according to the invention for preparing a micro-particulate obtained by ionotrophic gelification, by micronizing a feeding solution having a higher degree of viscosity with an orifice of larger size.

A first aqueous/alcoholic solution of 0.4% w/v HPMC (Cigenmann-Veronelli; Milan) was prepared, in which for each liter of solution, 4 g of HPMC were dissolved in 400 ml of EtOH and then 600 ml of water were added. A second aqueous solution of 1% w/v lysozyme (Belovo; Belgium) and 4% w/v sodium alginate (Quinsdao; Cina) was prepared, in which for each liter of solution, 10 g of lysozyme were dissolved in 1 litre of distilled water; 40 g of sodium alginate (Quinsdao; China) was then added and solubilized by homogenization. A feeding solution (hereinafter indicated by C) was then prepared, in which for each liter of solution, 547 ml of the solution A were mixed with 453 ml of the solution B. A collecting liquid was then pre-arranged in the gelification chamber (hereinafter referred to as solution D) consisting of an aqueous solution of 0.1% w/v chitosan (Quinsdao, Cina) and 15% w/v anhydrous $CaCl_2$ (Carlo Erba) in which for each liter of solution D, 1 g of chitosan was dissolved in one liter of water acidified with 2.5% v/v acetic acid. 150 g of anhydrous $CaCl_2$ were then added and solubilized.

Set-Up Condition of the Apparatus:
Feeding solution volume: 1.5 liter,
Collecting liquid volume: 1.5 liter,
Nebulization orifice: 0.30 mm (larger diameter),
Height of nebulization spread: 30 cm,
Input pressure of the nebulizing unit: 4 bars,
Feeding solution pump pressure: 1.5 bars,
Timing conditions:
nebulization pulse length: 0.5 sec,
pause between two nebulization pulses: 3 sec,
Gelification chamber rotation speed: 35 rpm The nebulization of the feeding solution was conducted through the above-described facility. The collecting liquid (solution D) was prepared in the gelification chamber kept in rotation. The feeding solution was pre-arranged in reservoir 1. The pneumatic circuits were then opened and the nebulizing unit actuated by previously setting the pressure and timing values as indicated above. One liter of feeding solution was nebulized during a period of about 15 minutes. At the end of the process, a semi-finished product consisting of micro-particles of calcium alginate, HPMC and chitosan containing lysozyme, suspended in the solution D, was obtained. The semi-finished product was then treated to obtain a dry product. More precisely, the semi-finished product was subjected in series to centrifugation, washings in absolute ethanol, pressurized filtration and drying at 37° C.

Example 3

Application of the apparatus according to the invention for preparing a micro-particulate obtained by ionotrophic gelification, by micronizing a feeding solution having a lower degree of viscosity with an orifice of smaller size.

A first aqueous/alcoholic solution of 0.4% w/v HPMC (Cigenmann-Veronelli; Milan) was prepared, in which for each liter of solution, 4 g of HPMC were dissoluted in 400 ml of EtOH and 600 ml of water were then added. A second aqueous solution of 1% w/v lysozyme (Belovo) and 2% w/v sodium alginate (Quinsdao; China) was prepared, in which for each liter of solution, 10 g of lysozyme were dissolved in 1 liter of distilled water; 20 g of sodium alginate (Quinsdao; China) was then added and solubilized by homogenization. A feeding solution (hereinafter indicated by C) was then prepared, in which for each liter of solution, 547 ml of the solution A were mixed with 453 ml of the solution B. A collecting liquid was then pre-arranged in the gelification chamber (hereinafter referred to as solution D) consisting of an aqueous solution of 0.1% w/v chitosan (Quinsdao, China) and 15% w/v anhydrous $CaCl_2$ (Carlo Erba), in which for each liter of solution D, 1 g of chitosan was dissolved in one liter of water acidified with 2.5% v/v acetic acid. 150 g of anhydrous $CaCl_2$ were then added and solubilized.

Set-Up Condition of the Apparatus

Feeding solution volume: 1 liter,

Collecting liquid volume: 1.5 liter,

Nebulization orifice: 0.20 mm (smaller diameter),

Height of nebulization spread: 30 cm,

Input pressure of the nebulizing unit: 4 bars,

Feeding solution pump pressure: 2.5 bars,

Timing conditions:

nebulization pulse length: 0.5 sec, pause between two nebulization pulses: 2.5 sec, Gelification chamber rotation speed: 20 rpm.

The nebulization of the feeding solution was conducted through the above-described apparatus. The collecting liquid (solution D) was prepared in the gelification chamber kept in rotation. The feeding solution was pre-arranged in reservoir 1. The compressed air circuit was then opened and the nebulizing unit actuated by previously setting the pressure and timing values as indicated above. One liter of feeding solution was nebulized during a period of about 30 minutes. At the end of the process, a semi-finished product consisting of micro-particles of calcium alginate, HPMC and chitosan containing lysozyme, suspended in the solution D, was obtained. The semi-finished product was then treated to obtain a dry product. More precisely, the semi-finished product was subjected in series to centrifugation, washings in absolute ethanol, pressurized filtration and drying at 37° C.

Example 4

Application of the apparatus according to the invention for preparing micro-particles obtained by ionotrophic gelification, by micronizing a feeding solution having a lower degree of viscosity with an orifice of larger size.

A first aqueous/alcoholic solution of 0.4% w/v HPMC (Cigenmann-Veronelli; Milan) was prepared, in which for each liter of solution, 4 g of HPMC were dissolved in 400 ml of EtOH and 600 ml of water were then added. A second aqueous solution of 1% w/v lysozyme (Belovo) and 2% w/v sodium alginate (Quinsdao; China) was prepared, in which for each liter of solution, 10 g of lysozyme were dissolved in 1 liter of distilled water; 20 g of sodium alginate (Quinsdao; China) was then added and solubilized by homogenization. A feeding solution (hereinafter indicated by C) was then prepared, in which for each liter of solution, 547 ml of the solution A were mixed with 453 ml of the solution B. A collecting liquid was then pre-arranged in the gelification chamber (hereinafter referred to as solution D) consisting of an aqueous solution of 0.1% w/v chitosan (Quinsdao, China) and 15% w/v anhydrous $CaCl_2$ (Carlo Erba), in which for each liter of solution D, 1 g of chitosan was dissolved in one liter of water acidified with 2.5% v/v acetic acid. 150 g of anhydrous $CaCl_2$ were then added and solubilized.

Set-Up Condition of the Apparatus:
Feeding solution volume: 1.5 liter,
Collecting liquid volume: 1.5 liter,
Nebulization orifice: 0.30 mm (larger diameter),
Height of nebulization spread: 30 cm,
Input pressure of the nebulizing unit: 4 bars,
Feeding solution pump pressure: 2 bars,
Timing conditions:
nebulization pulse length: 0.5 sec,
pause between two nebulization pulses: 2.5 sec,
Gelification chamber rotation speed: 20 rpm.

The nebulization of the feeding solution was conducted through the above-described apparatus. The collecting liquid (solution D) was prepared in the gelification chamber kept in rotation. The feeding solution was pre-arranged in reservoir 1. The compressed air circuit was then opened and the nebulizing unit actuated by previously setting the pressure and timing values as indicated above. One liter of feeding solution was nebulized during a period of about 30 minutes. At the end of the process, a semi-finished product consisting of microparticles of calcium alginate, HPMC and chitosan containing lysozyme, suspended in the solution D, was obtained. The semi-finished product was then treated to obtain a dry product. More precisely, the semi-finished product was subjected in series to centrifugation, washings in absolute ethanol, pressurized filtration and drying at 37° C.

A characterization of the micro-particles obtained in the examples 1, 2, 3, 4 is disclosed below. More precisely, the micro-particles were subjected to a rheological analysis and compared for determining the dimensional distribution, the resting angle, the lysozyme release at pH 3 and pH 8 as described below.

Rheological Analysis

The rheological analyses were performed by a Rheostress Haake RS 150 rheometer with grained parallel plates. The rheological analyses were performed by analyzing two types of feeding solution, a first one (solution A) of a low degree of viscosity and a second one (solution B) of high degree of viscosity.

The feeding solution was obtained by mixing a solution 1 (2% w/v alginate and 1% w/v lysozyme) with a solution 2 (0.4% HPMC w/v in 40% v/v ethanol). The final concentration of the single components in the feeding solution A (feeding solution 1+feeding solution 2) is as follows:

| Feeding solution A (viscosity = feeding solutions of Examples 3 and 4) | Initial concentration of solutions 1 and 2 | Final concentration of feeding solution A |
|---|---|---|
| Solution 1 | Alginate 2% w/v Lysozyme 1% w/v | Alginate 1.09% w/v Lysozyme 0.547% w/v |
| Solution 2 | HPMC 0.4% w/v Ethanol 40% v/v | HPMC 0.219% w/v Ethanol 21.88% v/v |

On the other hand, the feeding solution B was obtained by mixing a solution 1 (4% w/v alginate and 1% w/v lysozyme, as reported in the previously described example 1) with a solution 2 (0.4% w/v HPMC in 40% v/v ethanol). The final concentration of the single components in the second liquid is as follows:

| Feeding solution B (viscosity = feeding solutions of examples 1 and 2) | Initial concentration of solutions 1 and 2 | Final concentration of feeding solution B |
|---|---|---|
| Solution 1 | Alginate 4% w/v Lysozyme 1% w/v | Alginate 2.18% w/v Lysozyme 0.547% w/v |
| Solution 2 | HPMC 0.4% w/v Ethanol 40% v/v | HPMC 0.219% w/v Ethanol 21.88% v/v |

To test the influence of the single components on the rheological behavior of the whole system, solutions obtained by subtracting one or more components from the feeding solutions were analyzed:

| Sample | Composition |
|---|---|
| 1 | Feeding solution A (1.09% w/v alginate; 0.547% w/v lysozyme, 0.219% w/v HPMC, 21.88% v/v ethanol) |
| 2 | Feeding solution B (2.18% w/v alginate, 0.547% w/v lysozyme, 0.219% w/v HPMC, 21.88% v/v ethanol) |
| 3-4 | 1.09 or 2.19% w/v alginate, 0.547% w/v lysozyme, 21.88% v/v ethanol |
| 5-6 | 1.09 or 2.19% w/v alginate, 0.547% w/v lysozyme |
| 7-8 | 1.09 or 2.19% w/v alginate, 0.219% w/v HPMC, 21.88% v/v ethanol |
| 9-10 | 1.09 or 2.19% w/v alginate, 21.88% v/v ethanol |
| 11-12 | Alginate 1.09 or 2.19% w/v |

Results Obtained at a Continuous Shear Stress

Figure 13:
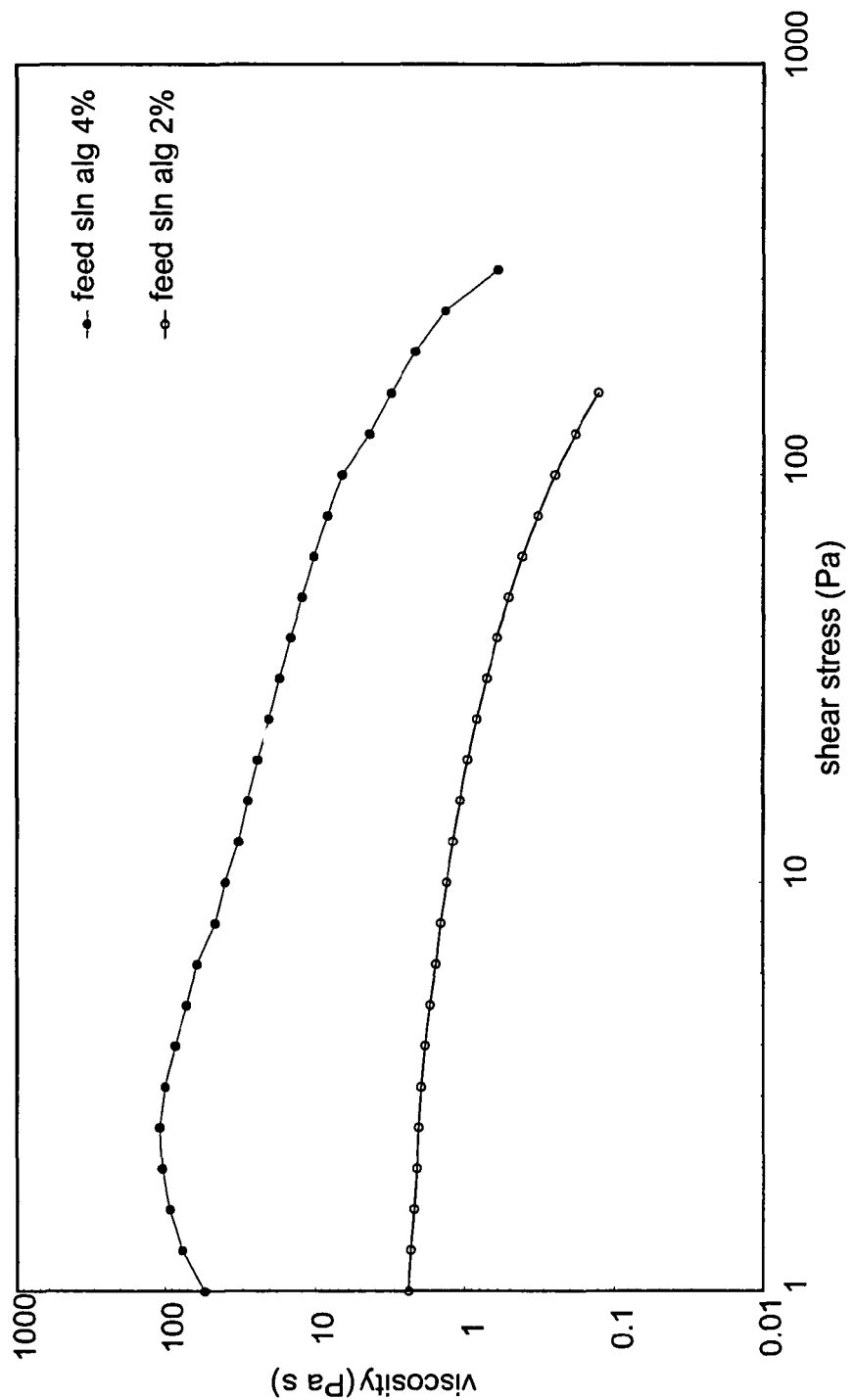
FIGS. 13 to 17 show curves related to the rheological analysis of the batches related to the FIGS. 3 and 6.

In FIG. 13, the viscosity values of examples 1 and 2 are shown if measured within a shear stress range of 1-300 Pa. The viscosity values obtained are as follows (shear stress=1 Pa; temp.=25° C.):

sample 1 (feeding solution A, viscosities=feeding solutions of examples 3 and 4): 2.38 Pa·s;
sample 2 (feeding solution A, viscosities=feeding solutions of examples 1 and 2): 53.58 Pa·s.

Figure 14:
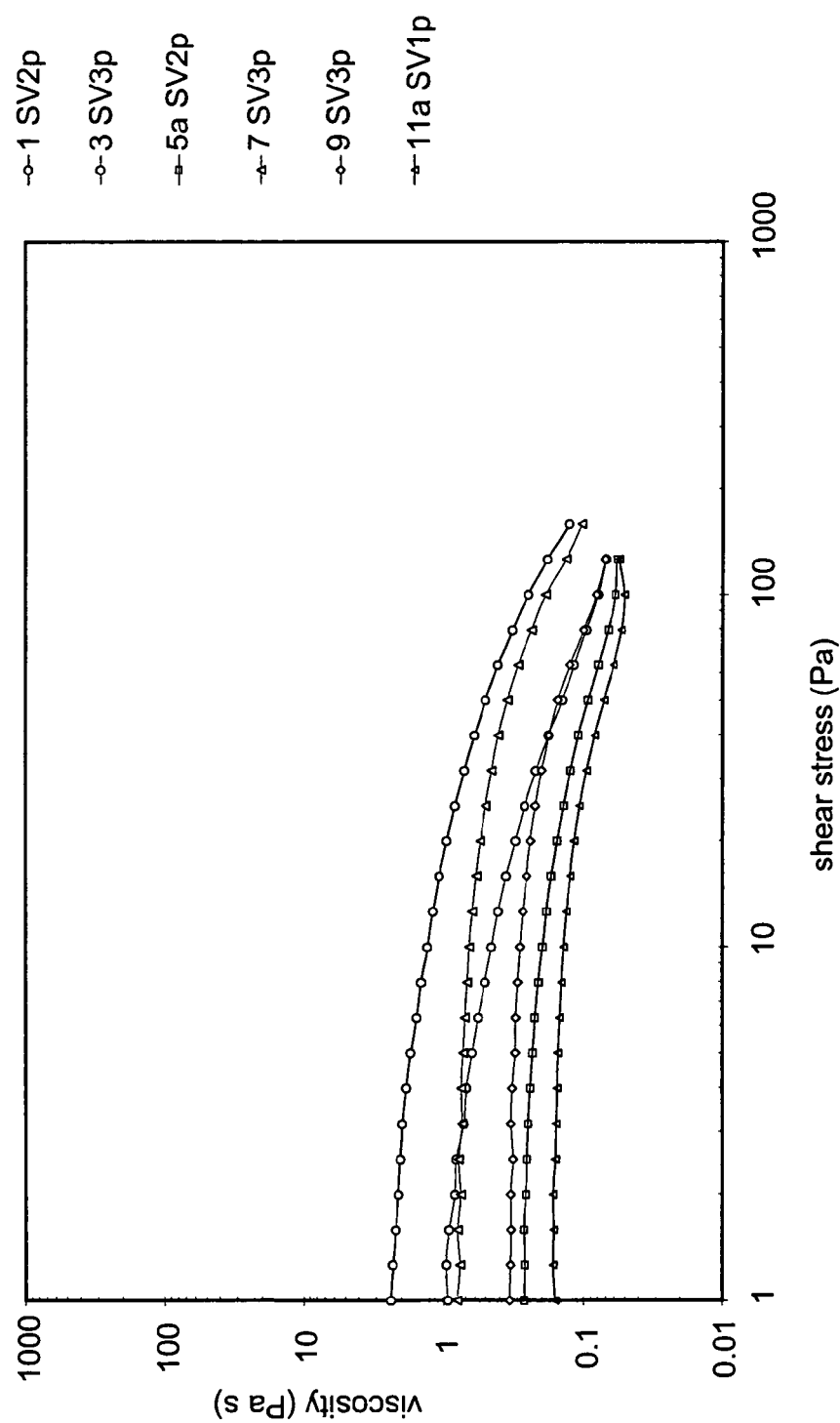
Figure 16:
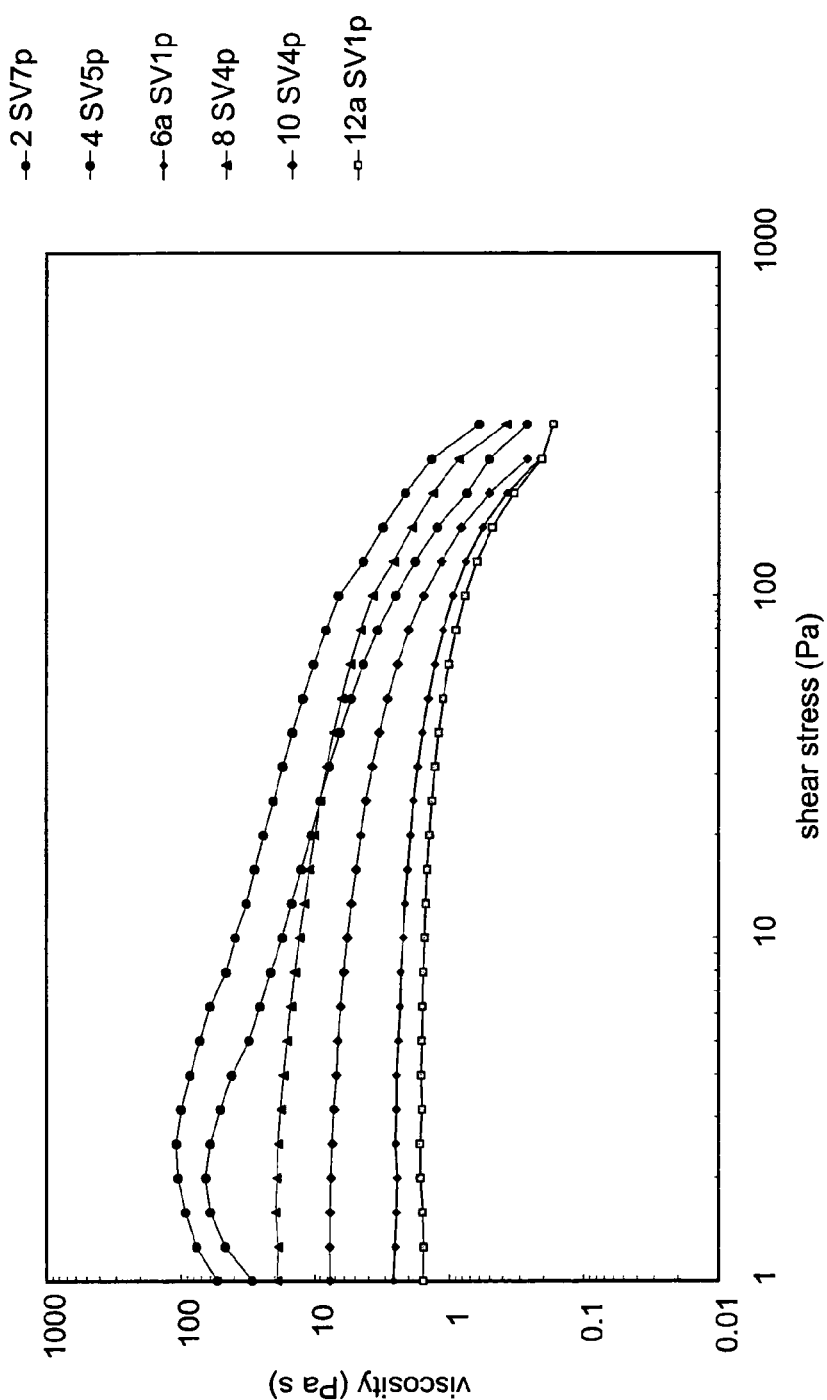

In FIG. 14 the behavior of sample 1 and of the solutions obtained by subtracting one or more components from such a solution is shown. From the viscosity values as compared to a solution of alginate alone at the same concentration. The trend of the curves registered for the different systems, shows a clear effect of the presence of lysozyme on the behavior of the final system, characterized by the decrease of viscosity values observed at high shear stress. Similarly, in FIG. 16 the viscosity trend related to sample 2 and of the derivated systems is shown. Also in this case, the presence of lysozyme (associated with ethanol) influences the curve trend of the final system: indeed, in the range 1-1000 Pa, lysozyme is responsible of an initial, gradual viscosity increase followed by a rapid decrease of such a value at high shear stress.

Results Obtained at a Fluctuating Shear Stress

Figure 15:
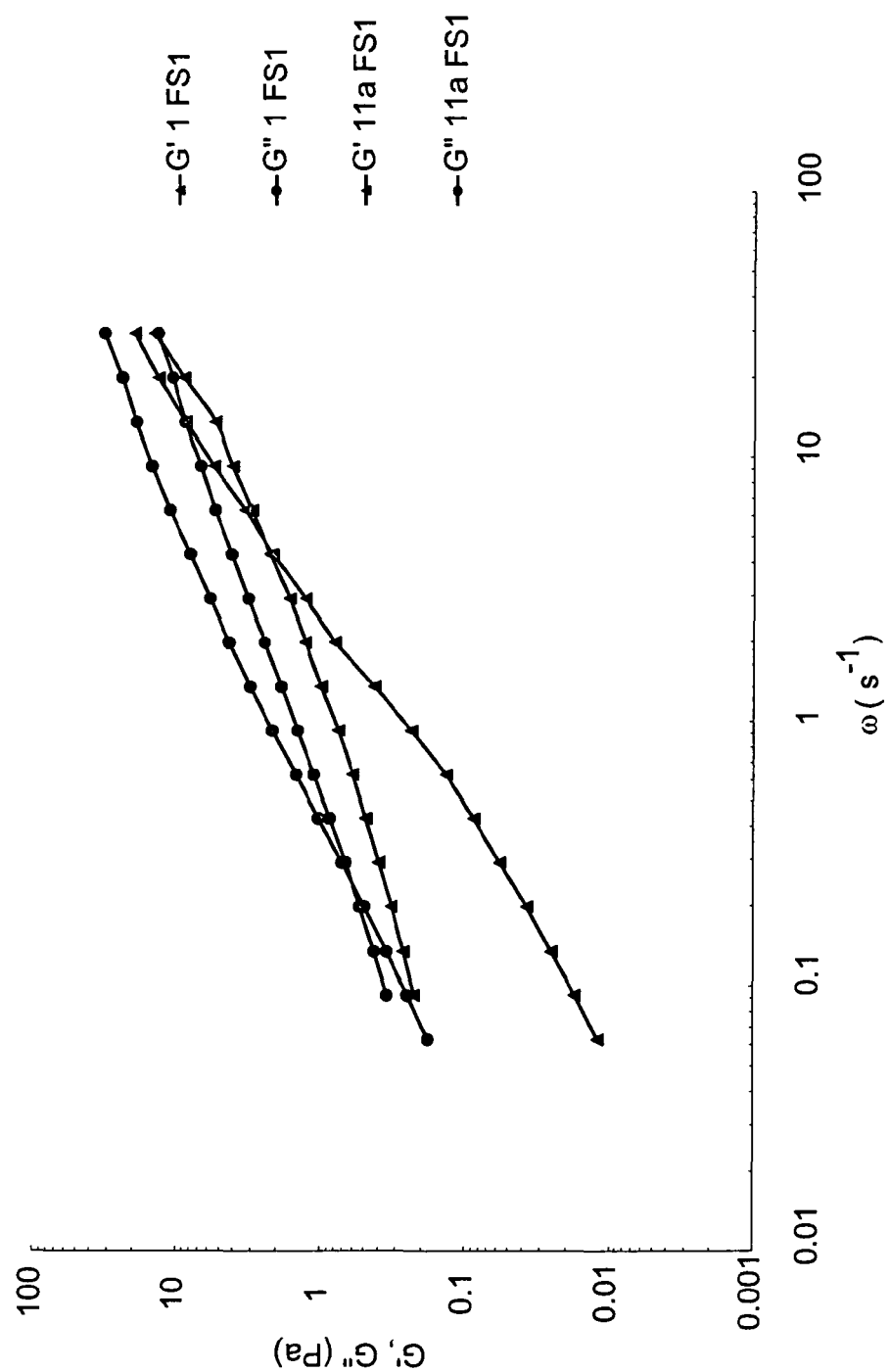
Figure 17:
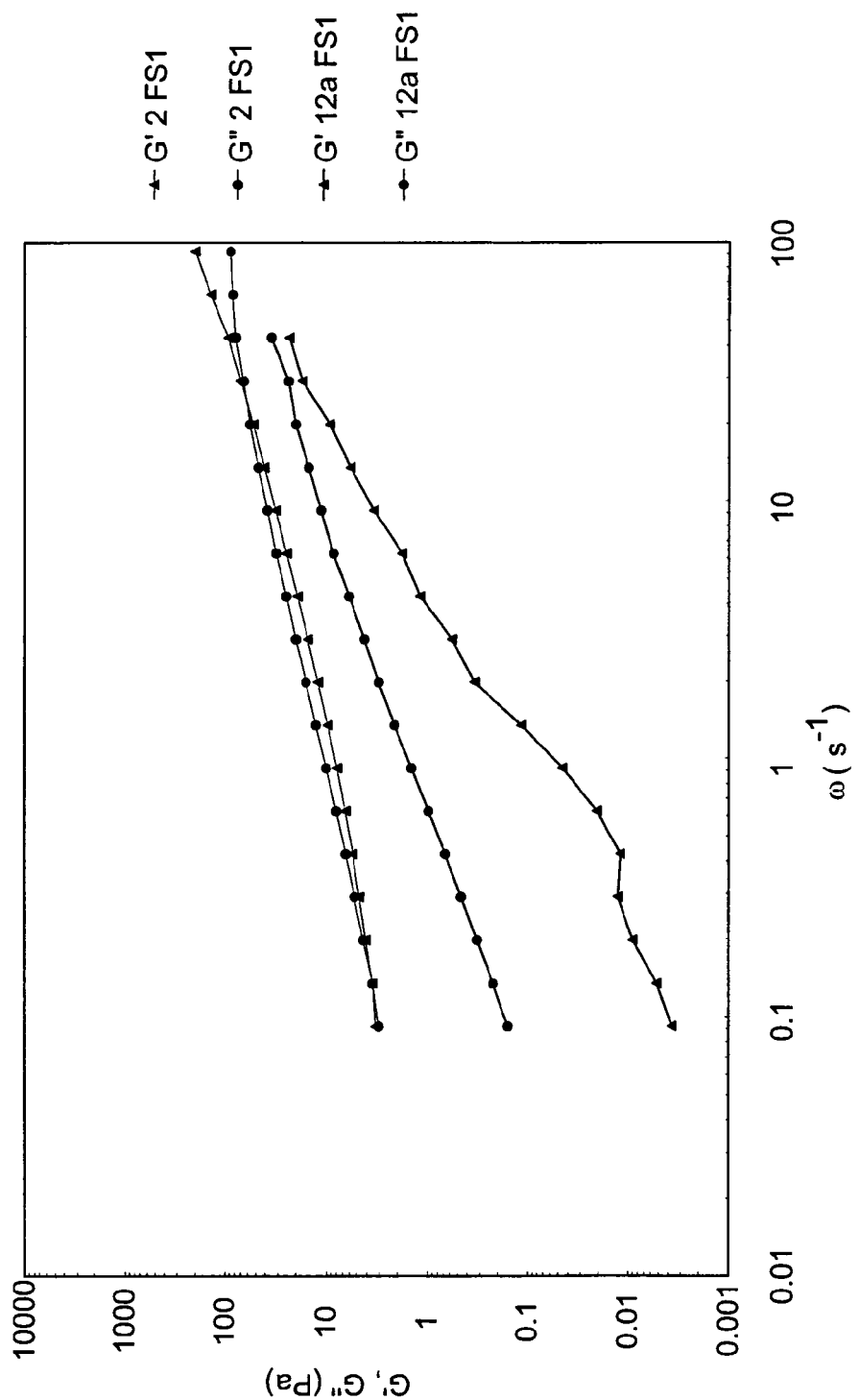

FIGS. 15 and 17 show the trend of the elastic component G' and of the viscous component G", related to the feeding solutions A and B, compared with the corresponding solutions of alginate (1.09% and 2.18% w/v). For both feeding solutions, G' values are maintained high throughout the stress range with a trend almost superimposable to G". Therefore, this means a trend approaching the "solid-like" type and is thus amenable to a partial co-organization of the different components of the system, as apparent from the comparison with the values of the solutions of alginate alone.

Dimensional Analysis

Dimensional analyses of the batches of alginate micro-particles coated with chitosan containing lysozyme were performed with an instrument commercially known as Accusizer 780/AS Autodiluter. Such an instrument counts and measures the particle dimensions by using the Single-Optical Sensing system (SPOS), also known as Optical Particle Counting (OPC). The four batches of micro-particles obtained from examples 1-4 were sieved with a 400 μm inox steel square-mesh sieve. The powder retained by the sieve (size larger than 400 μm) was quantified for each batch and inserted in Table 1. The batch of example 3, with 17% of retained material, is the one that had the highest amount of coarse particles. In this regard, table 1 relates to the amounts and percentage of powder retained by the sieve. The so-treated powders were then suspended in the desired medium to carry out the dimensional analysis. Regarding the samples without swelling, a proper amount of powder was dispersed in ultra-pure water ($\rho$=18.2 MΩ/cm) and the suspension was immediately subjected to grain size distribution analysis. On the other hand, the others samples were suspended in the desired medium, swelled for 12 hrs. at room temperature without stirring and then analyzed. A series of samples was swelled with ultra-pure water, while another series with 0.1 M phosphate buffer at pH 8.

TABLE 1

Amount and percentage of powder retained by the sieve.

| Batch | Percentage of powder retained by the sieve |
|---|---|
| Example 1 | 3.0% |
| Example 2 | 5.0% |
| Example 3 | 17.7% |
| Example 4 | 7.1% |

The results of the dimensional analyses of the four batches of alginate-chitosan micro-particles containing lysozyme are shown in Table 2. More precisely, such a table shows the dimensional analyses related to the particles measured without swelling, after swelling in water and after swelling in PBS. The dimensional analyses of the batches of alginate-chitosan micro-particles containing lysozyme were performed with an Accusizer 780/AD Autodiluter. The instrument counts and measures the particle dimensions by using the Single-Particle Optical Sensing (SPOS) system, also known as Optical Particle Counting (OPC). In practice, the software calculates the surface area or volume of each particle considering it to be spherical in shape (it calculates for each dimensional class and multiplies by the total number of particles having that given diameter), then calculates the total area or volume (i.e. the area or volume of all the particles analyzed during the measurement) and reports the percentage of area or volume of each diameter with respect to total. This way of expressing the result aids to understand the percentage contribute that each single population of the distribution exerts on the total area or volume of the investigated sample. The most useful result is usually that by volume as it is directly related to the mass.

On the other hand, FIGS. 3 to 6 show the statistical distributions of the values related to volume-area and particle number of each batch. As apparent from these last figures, the dimensional analyses of the four batches showed (before swelling) almost wide distributions with, sometimes (batches 2, 3, 4), particles larger than 200 μm.

From the results, batch 1 is seen to be the best out of four, while batches 2, 3 and 4 are more poly-dispersed (out of these three, batch 3 has a wider distribution than the others). Swelling in deionized water does not change the average size and the dimensional distributions very much, which happens instead when swelling is performed in PBS. Indeed, an increase of the number of particles with smaller dimensions is noticed, which deforms the left part of the Gaussian. This phenomenon may be explained by considering that the phosphate of the buffer tends to destroy the particles of calcium alginate by subtracting calcium therefrom to form calcium phosphate. Even if this phenomenon may be partly blocked and/or slowed down by the presence of the polycation chitosan, the presence of phosphate may not be inferred to be able to destroy a certain amount of micro-particles (not perfectly covered by chitosan), thus forming small-sized debris detected as particles by the instrument. Another conceivable explanation is that the particles with dimensions lower than 2 microns (lower detection limit of the instrument, thus not detectable, once incubated in PBS increase in size, this time being detected by the instrument.

TABLE 2

Average diameters obtained from the dimensional analysis of the four batches of particles.

| Batch | Diameter | Without swelling | After swelling in $H_2O$ | After swelling in PBS |
|---|---|---|---|---|
| Ex. 1 | Number (%) | 16.67 ± 14.26 | 15.11 ± 11.38 | 16.59 ± 16.64 |
| | Area (%) | 44.66 ± 32.91 | 34.77 ± 24.10 | 63.58 ± 68.55 |
| | Volume (%) | 68.90 ± 61.11 | 51.47 ± 45.30 | 137.49 ± 125.53 |
| Ex. 2 | Number (%) | 24.20 ± 27.09 | 21.95 ± 23.20 | 10.74 ± 11.64 |
| | Area (%) | 94.41 ± 77.28 | 85.51 ± 71.13 | 56.76 ± 74.14 |
| | Volume (%) | 158.72 ± 108.83 | 144.67 ± 105.31 | 153.61 ± 136.32 |
| Ex. 3 | Number (%) | 13.34 ± 16.89 | 15.24 ± 18.21 | 8.94 ± 11.91 |
| | Area (%) | 90.86 ± 95.31 | 87.95 ± 87.96 | 78.71 ± 97.29 |
| | Volume (%) | 190.84 ± 132.19 | 175.92 ± 125.51 | 199.01 ± 142.03 |
| Ex. 4 | Number (%) | 11.59 ± 17.56 | 15.26 ± 20.22 | 11.12 ± 15.15 |
| | Area (%) | 99.19 ± 91.97 | 102.28 ± 96.61 | 125.86 ± 136.75 |
| | Volume (%) | 184.46 ± 122.71 | 189.79 ± 123.55 | 274.44 ± 131.70 |

Determination of the Resting Angle

Figure 7:
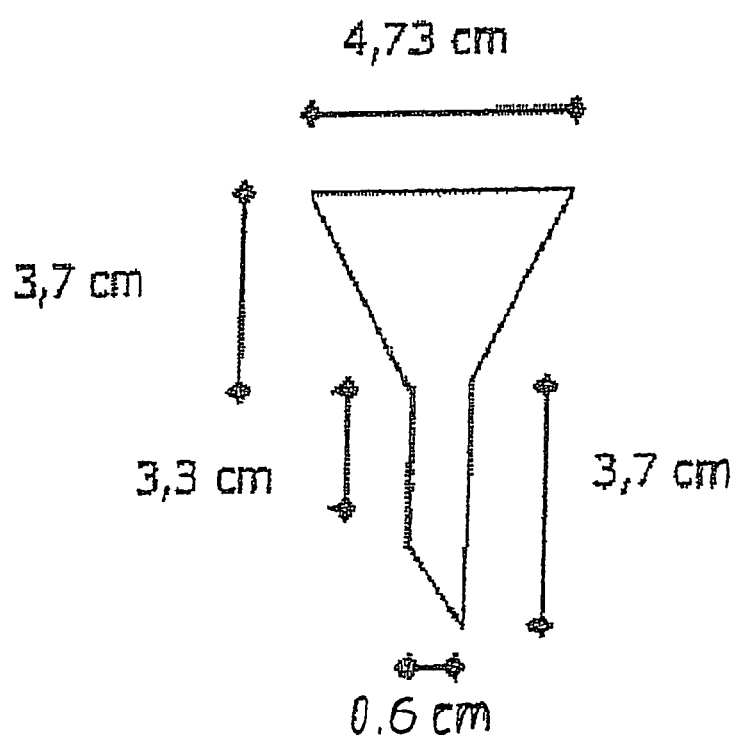
FIG. 7 is a diagrammatic view of the apparatus for measuring the resting angle related to the particles in FIGS. 3 to 6.
Figure 8:
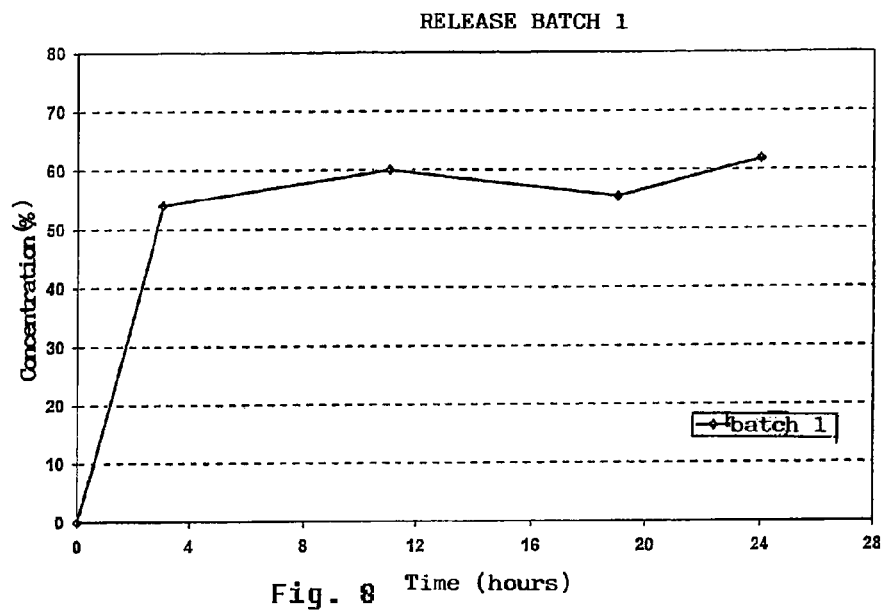
FIG. 8 shows the release curve of the biologically active substance related to the particles of the batch in FIG. 3.
Figure 9:
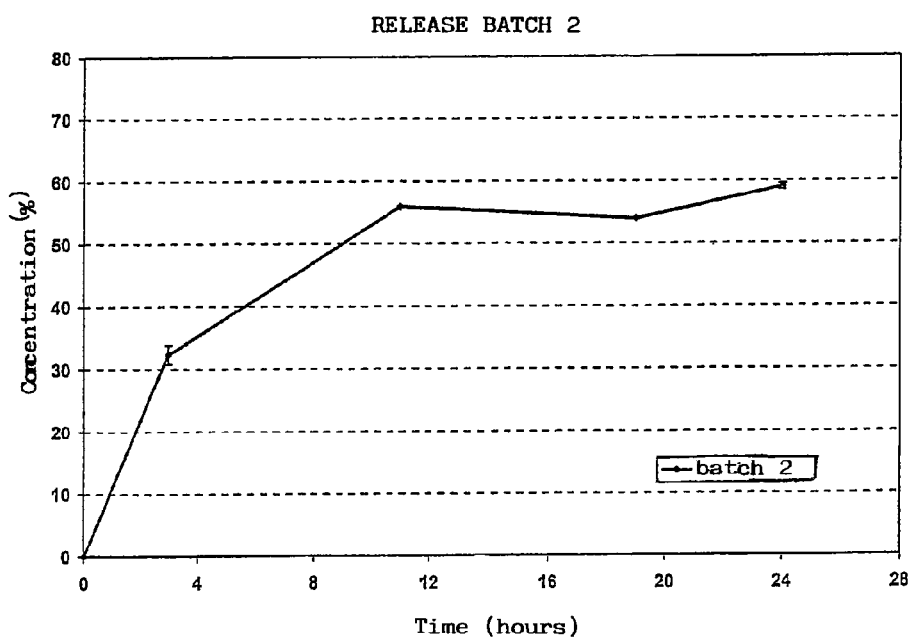
FIG. 9 shows the release curve of the biologically active substance related to the particles of the batch in FIG. 4.
Figure 10:
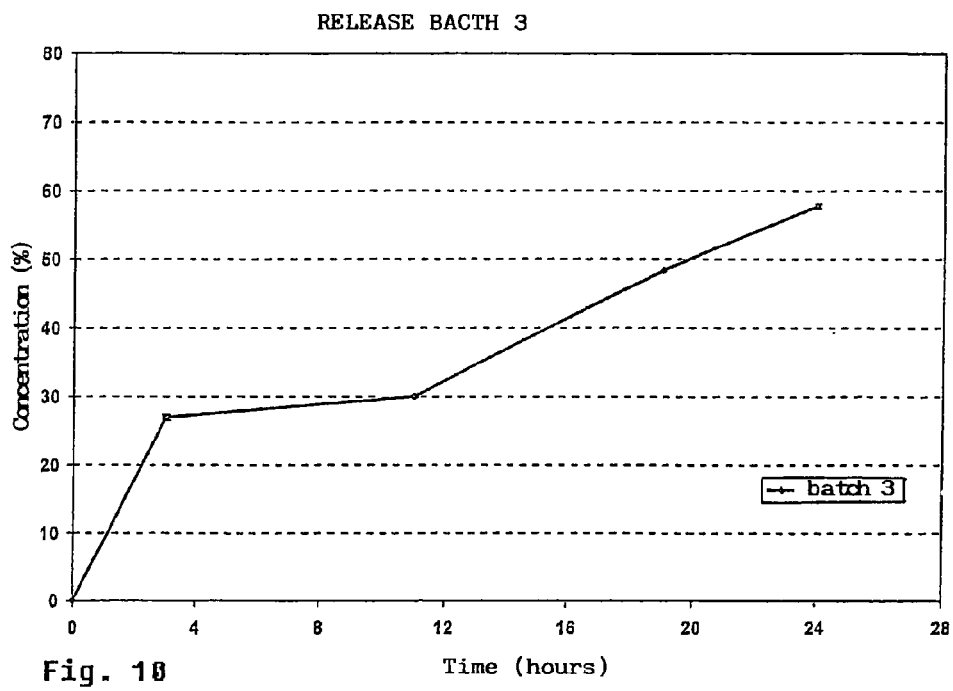
FIG. 10 shows the release curve of the biologically active substance related to the particles of the batch in FIG. 5.
Figure 11:
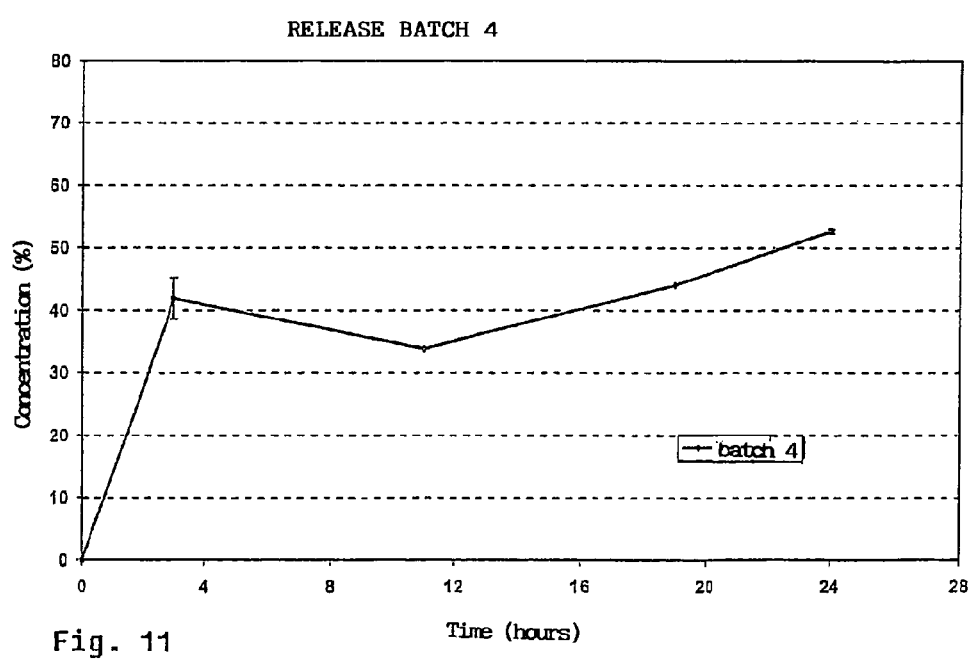
FIG. 11 shows the release curve of the biologically active substance related to the particles of the batch in FIG. 6.

The determination of the resting angle is a simple and fast method to obtain information about the powder flowability feature. The resting angle is one of the methods reported in the European Pharmacopeia for the characterization of pharmaceutical powders. The analysis according to this method consists in making the investigated powder flow through a funnel on a circular surface with a given diameter, thus forming a cone of powder. From the geometrical features of the cone (height, base diameter), the tangent of the angle from which the resting angle is obtained, is calculated. The size of the funnel used to perform the measurements is in FIG. 7, while table 3 below contains the final results of resting angle, performed in triplicate.

TABLE 3

| | Resting angle values. | | | |
| --- | --- | --- | --- | --- |
| | Batch 1 | Batch 2 | Batch 3 | Batch 4 |
| Resting angle (1) | 31.80° | 32.62° | 36.87° | 32.21° |
| Resting angle (2) | 32.21° | 32.21° | 38.31° | 32.21° |
| Resting angle (3) | 31.38° | 33.02° | 37.23° | 33.42° |
| Mean ± S.D. | 31.80° ± 0.42°* | 32.62° ± 0.41°* | 37.47° ± 0.75°** | 32.61° ± 0.70°* |

As apparent from the average values shown in Table 3, the powders related to batches 1, 2 and 4 are characterized by a resting angle of about 32° and have good flow characteristics. On the other hand, batch number 3 shows a higher resting angle (about 37.5°) but the flow characteristics are still considered favorable. The highest resting angle value is well related to the shape and surface morphology of the particles. Indeed, by means of the microscopic analysis, batch 3 has highlighted irregularly shaped particles with a particularly wrinkled surface.

Analysis of the Released Lysozym Content

For the analysis of the amount of lysozyme released from the micro-particles, the method BCA was employed, which uses bicinchoninic acid (BCA kits) to quantify the amount of proteins o peptides, by means of a colorimetric reaction. The method is based on the stoichiometric reduction of $Cu^{2+}$ to $Cu^+$ by peptidic compounds. The bicinchoninic acid chelates $Cu^+$ with high specificity thus forming a purple hydrosoluble complex. The reaction mixture is incubated at 60° C., as the temperature promotes the complexation. Even if very slowly, the reaction continues over time also after the cooling, therefore the measurement need to be carried out at given temperatures and times. The analyses were performed by spectrophotometry (562 nm) and the obtaining concentrations through a calibration curve. The reaction mixture is prepared by mixing bicinchoninic acid and copper sulfate in a 98/2 ratio (blue-green). The bicinchoninic acid solution is added to standards and samples in a 1:1 ratio. They are incubated at 60° C. for 1 hour and, after cooling, the measurements are performed. The releases were performed in a glycine buffer at pH 3 (24 hrs.), for simulating the passage in the gastric environment, and then in a phosphate buffer at pH 8 (24 hrs.) thus simulating the intestinal environment. The releases were performed at 37° C. The contents of lysozyme in the four batches of micro-particles are shown in table 4. The amounts of lysozyme are expressed as percentage of lysozyme loaded into the micro-particles.

TABLE 4

| Amount percent of lysozyme released from the micro-particles at 37° C. | | | | |
| --- | --- | --- | --- | --- |
| | Batch 1 | Batch 2 | Batch 3 | Batch 4 |
| % Amount released in 24 hrs. at pH 3 | 6.7 | 2.9 | 5.1 | 7.7 |
| % Amount released in 24 hrs. at pH 8 | 61.8 | 59.0 | 57.8 | 52.6 |
| Total % amount | 68.5 | 61.9 | 62.9 | 60.3 |

Figure 12:
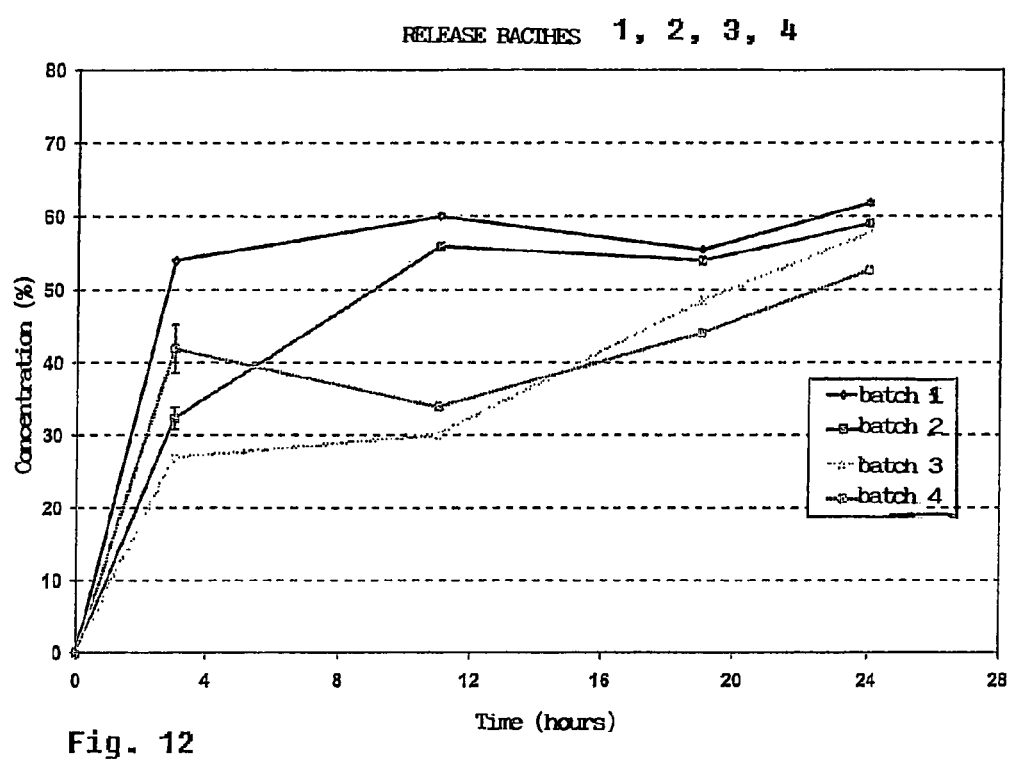
FIG. 12 shows the curves related to the FIGS. 8 to 11 together.

The curves related to the releases of lysozyme, at pH 8, from the particles related to the batches of examples 1-4 are shown in FIGS. 8 to 11, respectively. On the other hand, FIG. 12 shows these release curves in a single diagram in order to allow a faster comparison. Batches 1 and 2 were produced with high viscosity alginate while the 3 and 4 batches with low viscosity alginate. Of course, the parameters which may affect the release are many and the viscosity of the starting alginate is certainly an important one. In addition to viscosity, the average size, the dimensional distribution and the morphological features play a role in the release kinetic. Indeed, batch 1 releases very quickly and already within 3 hrs. the maximum amount of the lysozyme released during 24 hrs. is virtually obtained. Of course, this is partly due to the low size of the particles but also the viscosity of the alginate solution may have an effect. The particles of batch 2 release the maximum amount of lysozyme within 9 hrs., while a more sustained release is seen for batch 3. The latter indeed releases during all the 24 hrs. considered. The particles of batch 4 also release during all the 24 hrs. even if in a less linear manner. The releases of batches 3 and 4 may be explained with the low viscosities of the alginate solutions.

Microscopic Analysis of the Particles

The morphological analyses were performed by scanning electron microscopy (SEM) using a Philips XL30 microscope (Philips Electron Optics, Heindoven; NL). For SEM analysis, a small amount of powder was adhered on an aluminium stub provided with an adhesive carbon support and then subjected to spray coating with gold before the analysis (EMITECH K-550X sputter coater Ashford, Kent; UK).

Depending on the morphological characterization only, batches 1 and 2 are better than batches 3 and 4. In particular, the shape of the particles of the first two batches is more comparable to the spherical one as compared to the others, even if the particles of batch 2 are however more similar to batches 3 and 4 than those of batch 1. This behavior is related to the viscosity of the alginate solutions used for producing the different batches. Indeed, batches 1 and 2 were produced with a higher viscosity alginate (~50-100 Pa·s) and, considering the high spraying pressure of the production system, a higher viscosity may be assumed to cause the particle to keep the size and shape of the drop formed during nebulization. On the other hand, in the case of a lower viscosity (~2 Pa·s), the drops—theoretically also smaller (generally speaking, the nebulization of a lower viscosity solution should generate drops, therefore smaller particles)—deformate and aggregate at the time of the impact with the surface of the gelifying solution, thus forming large particles which are irregular in shape and surface. This assumption is confirmed by the dimensions of batches 3 and 4 (batch 3, 191 µm; batch 4, 184 µm), which are higher than those of batches 1 and 2 (batch 1, 69 µm; batch 2, 159 µm).

Provided that optimal particle shape and size strictly depend on the application of the particulate, batches 3 and 4 are still interesting due to their lower bulk density and lower aerodynamic diameter.

In more general terms, the facility according to the present invention has the feature of producing micrometric-sized particle, even from highly viscous solutions (Exp1 and 2: about 100 Pa·s). Indeed, from 82 and 97% of the particles produced had dimensions smaller than 400 µm (batches sieving data). It is worth noting that a system of known type such as the spray dryer (supra), usually process solutions with viscosities not higher than 0.25 Pa·s, more than two magnitude orders lower than those processed by the facility object of the present invention. It is worth noting that the processing times are rather reduced in favour of an industrial scale utilization. Indeed, with the described facility, the average processing times are around 2 liters per hour (batch 1, 1.4 L/h; batch 2, 2 L/H; batch 3, 2 L/h; batch 4, 4 L/h).

The solutions envisaged for the present invention allow the intended objects to be achieved. In particular, the method and apparatus according to the invention advantageously allow the feeding solutions with varying viscosities within a wide range to be processed, differing from the traditionally employed processes. At the same time employing an air-less type nebulizing unit advantageously allows to increase the yield of the facility, thus leading to production costs advantageously reduced.

The invention claimed is:

1. Method for the production of micro-particles of polysaccharides, characterized in that it comprises the following steps:
   preparing a feeding solution containing at least one polysaccharidic polymer able to form micro-particle structures and at least one biologically active substance;
   preparing a gelifying liquid to collect nebulized jets of said feeding solution;
   pressurizing said feeding solution inside an air-less nebulizing unit;
   nebulizing said feeding solution through said air-less nebulizing unit in a way that it produces nebulized jets impacting the surface of said gelifying liquid.

2. Method according to claim 1, wherein said air-less nebulizing unit is operated in a way that it nebulizes said feeding solution in a pulsed mode.

3. Method according to claim 2, wherein said nebulizing unit is operated by means of a first pneumatic flow whose length and frequency are in a way that it operates said air-less nebulizing unit in said pulsed mode.

4. Method according to claim 3, wherein said feeding solution is prepared in a pressurized way inside said air-less nebulizing unit through a pump operated by means of a second pneumatic flow.

5. Method according to claim 4, wherein said first and said second pneumatic flows are generated by the same compressed air generating unit.

6. Method according to claim 5, wherein the air generated by said generating unit is treated in series in a drying unit and in a filter processing unit.

7. Method according to claim 1, wherein said gelifying liquid is kept in motion during the nebulization of said feeding solution.

8. Method according to claim 7, wherein said gelifying liquid is prepared inside a chamber of micro-incapsulation by gelification moved by a rotary platform.

9. Apparatus for producing polysaccharides particles, wherein said apparatus comprises:
   a reservoir for containing a feeding solution comprising at least one polysaccharidic polymer able to form micro-particle structures and at least one biologically active substance;
   a chamber of micro-incapsulation by gelification, suited to contain gelifying liquid;
   an air-less nebulizing unit operated by means of a first pneumatic flow, said nebulizing unit being pre-arranged with reference to said gelification chamber in a way that it generates nebulized jets impacting the surface of said gelifying liquid,
   wherein said nebulizing unit is hydraulically connected to the reservoir by interposing a pump operated by a second pneumatic flow to pressurize said feeding solution before the nebulization through said air-less unit.

10. Apparatus according to claim 9, wherein said apparatus comprises regulating means for regulating the length and the frequency of said first pneumatic flow in a way that said nebulizing unit is operated in a pulsed mode.

11. Apparatus according to claim 9, wherein said nebulizing unit comprises an interchangeable nozzle able to generate conical nebulized jets.

12. Apparatus according to claim 9, wherein said apparatus comprises moving means of said chamber of micro-encapsulation by gelification for moving the same during the nebulization of said feeding solution.

13. Apparatus according to claim 9, wherein said apparatus comprises a compressed air generating unit for generating said first and said second operating pneumatic flow, said apparatus comprising at least one unit for processing the air generated by said generating unit.

14. Apparatus according to claim 13, wherein said air processing unit comprises an air drying unit and an air filtering station downstream to said drying station.

* * * * *